United States Patent [19]

Greenwood

[11] Patent Number: 4,744,356
[45] Date of Patent: May 17, 1988

[54] DEMAND OXYGEN SUPPLY DEVICE

[76] Inventor: Eugene C. Greenwood, 4825 Coleman Rd., Richmond, Va. 23230

[21] Appl. No.: 835,215

[22] Filed: Mar. 3, 1986

[51] Int. Cl.⁴ .............................................. A61M 16/00
[52] U.S. Cl. ................................................. 128/204.26
[58] Field of Search ................... 128/204.23, 204.21, 128/102.22, 207.18, 205.24, 721, 722, 723, 204.24, 204.26

[56] References Cited

U.S. PATENT DOCUMENTS

| | | | |
|---|---|---|---|
| 2,912,979 | 11/1959 | Lieber | 128/204.23 |
| 3,097,639 | 7/1963 | Streimer | 128/721 |
| 3,191,595 | 6/1965 | Wilson | 128/204.23 |
| 3,267,935 | 8/1966 | Andreasen et al. | 128/200.17 |
| 3,400,712 | 9/1968 | Finan | 128/204.23 |
| 3,566,387 | 2/1971 | Schoener et al. | 128/204.26 |
| 3,782,368 | 1/1974 | Reibold | 128/721 |
| 3,831,596 | 8/1974 | Cavallo | 128/204.23 |
| 3,952,739 | 4/1976 | Cibulka | 128/204.23 |
| 4,155,357 | 5/1979 | Dahl | 128/202.22 |
| 4,336,590 | 6/1982 | Jacq et al. | 128/204.23 |
| 4,414,982 | 11/1983 | Durkan | 128/204.24 |
| 4,440,163 | 4/1984 | Spergel | 128/205.13 |
| 4,459,982 | 7/1984 | Fry | 128/204.23 |
| 4,461,293 | 7/1984 | Chen | 128/204.23 |
| 4,535,766 | 8/1985 | Baum | 128/204.23 |
| 4,538,604 | 9/1985 | Usry et al. | 128/204.23 |
| 4,546,793 | 10/1985 | Stupecky | 128/204.23 |
| 4,567,888 | 2/1986 | Robert et al. | 128/204.21 |
| 4,590,951 | 5/1986 | O'Connor | 128/204.23 |

FOREIGN PATENT DOCUMENTS 1492875  11/1977  United Kingdom ............... 128/721

Primary Examiner—Edward M. Coven
Assistant Examiner—J. P. Lacyk
Attorney, Agent, or Firm—Hall, Myers & Rose

[57] ABSTRACT

Provided herein is a demand breathing device including a motion sensitive sensor which sends signals corresponding to torso movement to a controller incorporating electronic differentiation to indicate the direction of torso movement corresponding to the expansion and retraction of inhalation and exhalation, respectively, and to energize a solenoid valve which interrupts oxygen flow during exhalation.

5 Claims, 1 Drawing Sheet

DEMAND OXYGEN SUPPLY DEVICE

TECHNICAL FIELD

This invention relates to controlling gas flow from a reservoir and, more particularly, to controlling the flow of supplemental oxygen from an oxygen-containing device to a person in need of a supplemental oxygen supply for medical purposes.

BACKGROUND OF THE INVENTION

In many cases of pulmonary disease and defects, patients are required to breathe supplemental oxygen in order to sustain physiologically adequate levels within the body. The need for oxygen supplementation is particularly acute with persons suffering from Chronic Obstructive Pulmonary Disease (COPD) such as emphysema. Diminished oxygen uptake into the body generally results from partial disability of the lungs caused by a variety of physiological ailments. Such disabilities lead their victims to require enrichment of atmospherically available oxygen. In view of the large number of persons in our society who require such oxygen supplementation, much effort has been dedicated to the development of devices which insure delivery of adequate supplemental oxygen to such persons.

The most common delivery system is a tank reservoir containing pressurized medical quality oxygen where the tank is outfitted with a flow regulator. The regulator constitutes a flow control valve which governs the rate of gas flow, i.e. volume, from the tank to a nasal canula or breathing mask. This type of conventional connection only permits control of flow to the patient's face, and the flow is constant during both inhalation and exhalation. It is well known to those involved in the medical field, either as a patient or health provider, that the cost of supplemental oxygen itself is high, exclusive of the adjunct delivery equipment. Accordingly, there has been an impetus to devise a delivery system in which the gaseous oxygen is supplied to the patient only upon demand by the patient, i.e. upon inhalation. First, such controlled delivery eliminates the discomfort created by continuous flow of oxygen into the nostrils even during exhalation. Secondly, and more importantly, a properly engineered demand oxygen supply device is economically desirable as it would eliminate the waste of oxygen during exhalation.

Exemplary prior art devices for detecting patient's oxygen demand relied on sensors placed under the person's nose or otherwise on a person's face. Such sensors may prove irritating to the patient. Alternatively, certain commercially available systems employ a sensor connected to a controller which in turn is connected to a solenoid valve on an oxygen tank. Upon sensing inhalation, by pressure changes, etc., the sensor signals the control apparatus which constitutes a switch, thereby energizing the solenoid, opening the valve and inducing oxygen flow. This arrangement may not provide oxygen to the user where there is a system failure. Additionally the foregoing arrangement may prove fatal in those situations where a high concentration of oxygen may be most desirable. This would occur where a person's breathing would have stopped or become so shallow so as to be undetectable by the sensor. In such a case the solenoid would not be energized and the valve would remain closed. Consequently, the enriched oxygen atmosphere is denied the patient when most needed.

It would be desirable to provide a reliable apparatus and method for supplying supplemental oxygen to a medical patient who is bedridden or ambulatory which provided a means to shut off oxygen flow only upon exhalation. It would also be desirable to provide the sensing means employed to control a shutoff valve which was positioned remote from the face of the user. Moreover, an advantageously designed control system would be small and compact so as not to overly interfere with normal perambulation.

SUMMARY OF THE INVENTION

It is an object of this invention to provide a demand breathing apparatus for association with supplementary oxygen sources.

Still another object of this invention is to overcome the problems associated with the prior art devices directed to flow regulation of supplemental oxygen to a person in need thereof.

Yet another object of this invention is to provide a convenient and reasonably safe demand breathing apparatus which activates a flow shut-off valve only during exhalation.

Still another object of this invention is a control mechanism which is worn on a user's torso thereby minimizing interference with the user's normal movements.

Still another object of this invention is to provide continuous oxygen flow in the event that the control means for flow regulation is not actuated.

These and other objects of the invention are satisfied by a gas flow controller for attachment to a gas reservoir featuring a solenoid valve capable of movement between an open position and a closed position where gas flow is stopped, a power supply electrically connected to said valve for moving said valve between the open and closed position, a motion sensitive detection sensor which generates an electrical signal corresponding to a particular motion condition, a controller in signal communication with said sensor and signal communication with said valve, said controller incorporating means for interpreting a sensor signal and means for generating a responsive signal thereto where said responsive signal causes said valve to move between the open and closed position.

To put it in other words, the instant invention contemplates a demand breathing apparatus which shuts off the flow of oxygen during exhalation but at all other times permits unimpeded oxygen flow. For COPD patients, this represents nearly a fifty percent oxygen volume savings and, therefore, cost savings.

At its most fundamental level, this invention is a sensor and switch. When the motion of exhalation is sensed and a corresponding signal relayed to the switch, a solenoid is energized causing the flow control valve to close thereby interrupting oxygen flow.

On a more descriptive level, the invention includes an electrical transducer sensor which detects torso expansion and contraction (corresponding to inhalation and exhalation, respectively). The transducer may be of numerous known types which generate a variable signal in response to certain conditions, namely, a change in direction of torso movement. The signal may be in the form of a change in resistance, current or voltage. The sensor's signal is fed to the associated controller which is sensitive to the signal produced by the sensor. The controller automatically compares the signal to a reference. Where the detected motion corresponds to exhalation, the controller energizes a solenoid which closes a valve on the oxygen tank flow regulator thereby stopping the flow of oxygen. Otherwise, the solenoid is not energized.

The invention provides the user with enhanced confidence as the controller energizes the solenoid only during the contraction or inward movement corresponding to exhalation of the torso. At all other times, the solenoid valve remains open so as not to deprive the user of needed oxygen, even when the sensor is removed entirely from the body.

The physical arrangement generally contemplated is where the sensor and controller are separate units worn on an adjustable belt or girdle around the torso. The controller is connected to a small rechargeable battery pack. The oxygen tank itself may be carried behind the user or, if small enough, may be strapped onto the belt whereby normal perambulation may be effectively sustained. The flow regulator on the tank has a solenoid valve for regulating oxygen flow which is electrically connected to the controller and a power supply.

These and other details of the invention will become apparent to one of ordinary skill in the art upon review of the following detailed description.

DETAILED DESCRIPTION OF THE ILLUSTRATED EMBODIMENT

Figure 1:
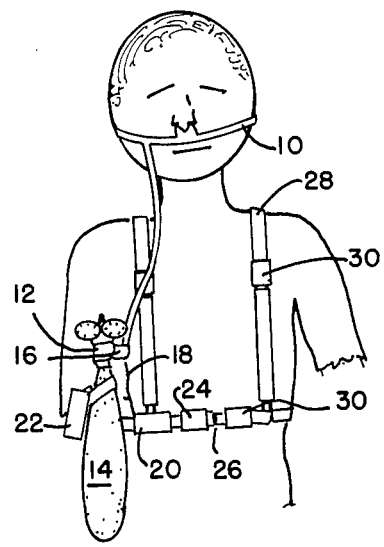
FIG. 1 is a front view of the invention.

In FIG. 1 is illustrated the invention's belt support structure, an exemplary configuration of the electronic components and the oxygen tank. Conventional nasal canula 10 is in pneumatic communication with oxygen tank 14. Flow regulator 12 is attached to the top of oxygen tank 14. The oxygen flow from tank 14 through regulator 12 to nasal canula 10 is controlled by conventional and commercially available spring bias open solenoid valve 16, such as Valve No. V2W491A40X, available from AIRMATIC-ALLIED SNAP-TITE INC., 185 Park Drive, Wilmington, Ohio 45177, or from one of many other companies. Solenoid valve 16 is connected by appropriate electrically conductive wires 18 to electronic controller 20 which in turn is connected by wires to portable battery pack 22. Electronic controller 20 is attached to torso belt 26. Torso belt 26 is adjustable by means of slide buckle 30 or Velcro fastening material. Suspenders 28, although not necessary, are provided to enhance positional stability of belt 26. Hence, suspenders or overshoulder belts 28 are adjustable as well as belt 26 by adjustment of buckle 30. The flexibility in use of the device is illustrated by the fact that since all elements are light weight, compact and water proof, they may be worn next to the skin or outside of clothing. Sensor 24 is also secured to belt 26 and is electrically connected to controller 20. The function of the various elements will now be described.

Electronic sensor 24 is preferably a strain-gauge load cell which is force/motion sensitive. Essentially, if pulled or pushed, the resistance of sensor 24 will change. By forcing a constant current through the sensor element, a voltage is produced whose value changes with the changing of sensor resistance. Thus, when expansion and contraction of the body occurs during inhalation and exhalation, there is a corresponding change in sensor voltage. This change is detected by electronic controller 20 and which determines the direction of motion. This aspect of the invention will be described in greater detail below. The physical characteristics of the strain gauge make it an appropriate choice. It is thin, flexible and may be designed to conform to any specific body contour. It is easily supported in a compact housing having dimensions of approximately $2 \times 1 \times \frac{1}{2}$ inches. When associated with a housing, it is easily secured to belt 26 which facilitates proper positioning. As is readily apparent to anyone skilled in the pulmonary arts, not only is there a wide variation of breathing patterns but, also, primary location for positioning a sensor on any particular patient will vary. It should be noted, however, that elementary component substitutions may be made. A linear variable differential transformer (LVDT) of either the DC-DC or AC-AC type (available from Automatic Timing & Controls Co. of King of Prussia, Pa.), a time modulated position transducer (available from Technar Incorporated of Arcadia, Calif.), a hall effect transducer, an angular displacement transducer (ADT), Piezo-electric crystal transducers, a conductive elastomeric transducer, or even a linear or rotary potentiometer may be employed as the motion sensor. Other commercial suppliers of such transducers constructed for analog or digital systems include Temposonics, Inc. a division of MTS Systems Corp., of Plainview, N.Y. and Trans Tek Incorporated of Ellington, Conn.

Some of these alternate sensors have a capacity, when linked with the appropriate microprocessor, to read out exactly how far the torso has moved and in what direction.

Figure 2:
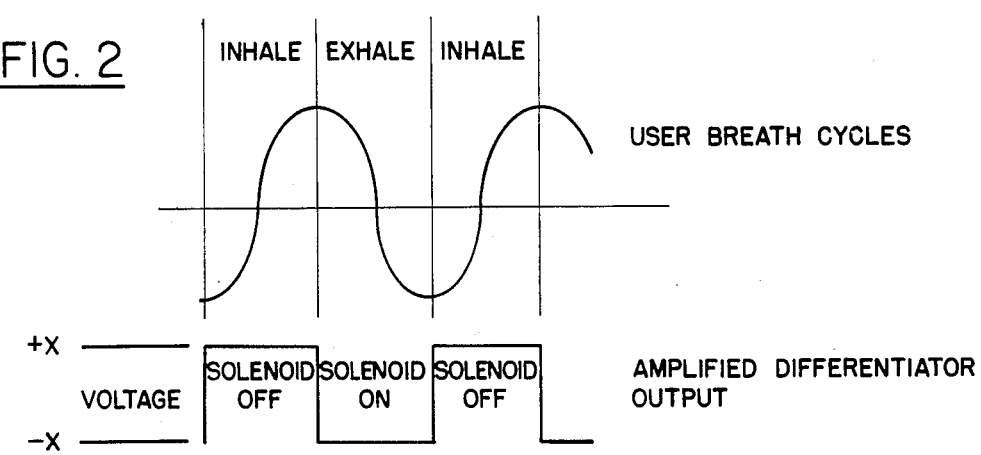
FIG. 2 is a graphical representation of the breathing/switching sequence of the instant invention.

The qualities, which must be possessed by any motion or position sensor device employed in this invention, are reliability and longevity. It is required that the switch operate during each breathing cycle, as depicted in FIG. 2. The preferred operating voltage is 6VDC and the power requirements for the switch equal to 0.5 watts pose only a diminutive danger to the user in the event of an "electrical accident". Many COPD patients breathe at a substantially increased rate (up to five times) but diminished amplitude from that experienced in normal pattern (see FIG. 2). The importance of the longevity and the reliability of the sensor is underscored by the fact that as many as three million cycles may be required in one year of operation.

The operation of the components is now described. During inhalation, the body expands in volume equal to the volume of the inhaled gas. Correspondingly, a substantially similar volume will be lost upon exhalation. Sensor 24 is able to detect the motion created by loss or gain of body volume. Sensor 24 is connected to electronic processing controller 20 which can be incorporated into a single unit therewith or, as illustrated, may be a discrete unit remote from the sensor. In order to reduce the number of components, sensor 24 and controller 20 should operate from the same power supply.

Figure 3:
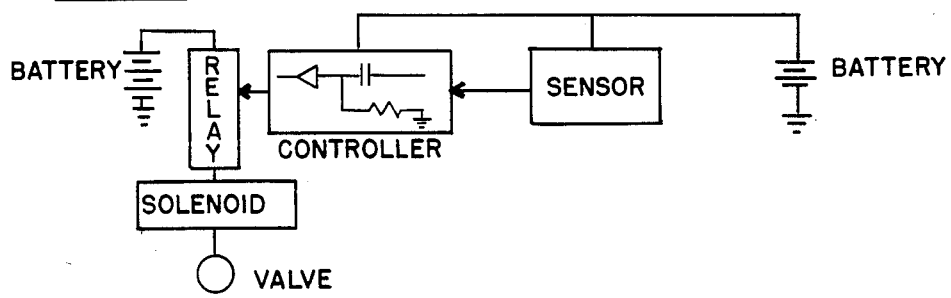
FIG. 3 is a schematic representation of the invention.

As already noted, the detection system may be either digital or analog based. Digital and analog, the two principal alternative constructions, for the sensor/controller will now be described where an analog system is preferred. In the analog embodiment represented by FIG. 3, a sensor's changes are detected by a differentiator circuit, a standard amplified grounded resistance capacitance circuit configuration. As the user breathes, the sensor resistance changes. By applying (or forcing, inducing) an electrical current of constant value to the sensor, a corresponding changing voltage is produced. This changing voltage is applied as an input to a differentiator circuit whose output is a voltage value indicative of the rate and polarity of change of the input voltage. The differentiator output may be amplified to produce a signal of sufficient power to drive the solenoid and close the oxygen valve during periods when the user is exhaling. However, making reference to FIG. 3, the amplified signal may be fed to a conventional relay which is energized thereby and which controls power to the solenoid. During all other phases of the breathing cycle, the sensor resistance remains unchanged or increases and the valve remains open. Consequently, for all times other than exhalation, the solenoid remains unenergized, the associated valve is open and the oxygen flow is unimpeded.

If the sensor is designed to have an increased resistance upon exhalation, then due to the inverse relationship of resistance to voltage, the voltage decreases.

Where digital, sensor 24 is interfaced with a microprocessor contained within controller 20. Sensor 24 is used as a frequency determining component of an oscillator circuit. Thus, as the resistance (or inductance, capacitance, whatever) of the sensor changes, the frequency of the oscillator changes. The oscillator output is fed to the timer-counter port in the microprocessor of controller 20.

If frequency increases or remains unchanged (corresponding to inhalation or stasis, respectively), the switch is off. However, upon exhalation, the frequency decreases, a negative change (delta) is detected and the microprocessor switches on, thereby activating the solenoid, closing the valve and blocking oxygen flow.

In the digital system, controller 20 has the capacity for comparing the signals produced by sensor 24, indicative of the sensed motion, which are fed into the timer controller 20. Controller 20 is capable of interrogation of the signal, of, for example, one hundred times a second based on a timer.

With either a digital or analog basis, controller 20, the sensor 24 system, is motion sensitive, not position sensitive. Should a user's body volume change or body change dimensions through some other influence such as ingestion, excretion, flatulence, indigestion, etc., the breathing control is still maintained with the present invention as it is still capable of sensing the relative motions of breathing.

Moving to the additional considerations for electronic solenoid valve 16 associated with regulator 12, it is connected to controller 20 in a manner where controller 20 causes the valve to open and close as regulated by the microprocessor. Valve 16 should be employable with compressed oxygen as well as liquid oxygen or other oxygen concentrators. It is also designed to operate in a pure oxygen atmosphere and is oxygen cleaned prior to installation. The power requirements of the system are critical for its operation.

The invention contemplates employment of batteries in systems generating either direct or alternating current. One arrangement, as illustrated, employs battery pack 22 including a nine volt battery for powering sensor 24 and controller 20 and a six volt battery to power solenoid valve 16. Preferably, these batteries are rechargeable. A conventional relay may be employed to connect the different power supplies. Battery pack 22 may constitute a single, sealed rechargable battery weighing approximately one pound which should ideally operate the invention for anywhere from a 12 to 24 hour period. Battery pack 22 may be strapped or attached to the oxygen tank as illustrated, or may be attached to other portions of the user's body and/or the invention.

Additional features may be incorporated with controller 20 such as a manual switch which allows the user to turn the control means off whereby an uninterrupted oxygen flow results. Another option of this invention would be to incorporate an electronic alarm system. In this event, it would be necessary to employ an additional electronic mechanism which would determine when a predetermined period of time had passed with no detectable change in the motion of the torso. For example, if no breathing had occurred during a predetermined 20 second interval, the alarm would sound due to the lack of any change in the voltage and/or current produced by the sensor.

Another feature would embody a timer which, if the solenoid valve remained closed for an unusually long period of time, say 10 seconds, the oxygen would automatically begin to flow full time.

These modifications and alterations of the invention should now be apparent to those of ordinary skill in the art and, accordingly, are intended to fall within the spirit and scope of the invention as defined in the following claims.

I claim:

1. In a gas flow regulator for attachment to a gas reservoir:

a solenoid valve capable of movement between an open position and a closed position where gas flow is stopped,
    a power supply electrically connected to said solenoid valve for moving said valve between the open and closed position,
    a motion sensitive detection sensor for detecting the direction of motion including an oscillator which generates an electrical signal corresponding to a particular motion direction detected,
    a controller in signal communication with said sensor and signal communication with said valve, said controller incorporating means for interpreting a change in the frequency of said sensor signal to read out the amount and direction of movement of the torso and means for generating a responsive signal thereto where said responsive signal causes said valve to move between the open and closed position.

2. A regulator according to claim 1 further including belt support means for attaching said sensor and controller to the torso of a user.

3. A device according to claim 1 wherein said power supply is a battery pack.

4. The gas flow regulator according to claim 1 where said motion sensitive detection sensor is affixed to a patient's body and where said soldenoid valve is energized only upon exhalation of air from the patient.

5. A regulator according to claim 4 where the motion sensitive detection sensor is a transducer.

* * * * *